United States Patent
Kambhampati et al.

(10) Patent No.: US 9,400,269 B2
(45) Date of Patent: Jul. 26, 2016

(54) SYSTEMS FOR DETECTING TARGET CHEMICALS AND METHODS FOR THEIR PREPARATION AND USE

(71) Applicant: The Royal Institution for the Advancement of Learning / McGill University, Montreal (CA)

(72) Inventors: Patanjali Kambhampati, Lachine (CA); Jonathan Ikola Saari, Zurich (SE); Nate Quitoriano, Montreal (CA); James Forbes, Ypsilanti, MI (US); Gordon Roberts, Montreal-West (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 0 days.

(21) Appl. No.: 14/492,811

(22) Filed: Sep. 22, 2014

(65) Prior Publication Data

US 2016/0084810 A1    Mar. 24, 2016

(51) Int. Cl.
*G01N 21/00* (2006.01)
*G01N 33/00* (2006.01)
*B05D 5/06* (2006.01)

(52) U.S. Cl.
CPC ............ *G01N 33/0009* (2013.01); *B05D 5/061* (2013.01)

(58) Field of Classification Search
CPC ............... G01N 33/0009; G01N 33/54373; G01N 21/7703; G01N 21/65; B05D 5/061; G01J 3/1895
See application file for complete search history.

(56) References Cited

U.S. PATENT DOCUMENTS

| | | | |
|---|---|---|---|
| 5,026,139 A | 6/1991 | Klainer et al. | |
| 5,094,958 A | 3/1992 | Klainer et al. | |
| 5,615,673 A * | 4/1997 | Berger | A61B 5/14532 356/301 |
| 5,684,297 A * | 11/1997 | Tardy | G01D 5/35383 250/227.14 |
| 5,814,565 A * | 9/1998 | Reichert | G01N 33/54373 385/12 |
| 6,694,067 B1 | 2/2004 | O'Keefe et al. | |
| 6,898,337 B2 * | 5/2005 | Averett | G01D 5/35303 385/12 |
| 7,228,017 B2 | 6/2007 | Xia et al. | |
| 7,420,663 B2 * | 9/2008 | Wang | G01J 3/02 356/326 |
| 7,595,882 B1 * | 9/2009 | Chen | G01N 21/0303 356/301 |

(Continued)

OTHER PUBLICATIONS

Méndez, A., "Fiber Bragg grating sensors: a market overview," Proc. SPIE 6619, Third European Workshop on Optical Fibre Sensors, vol. 6619, pp. 1-5 (2007).

(Continued)

*Primary Examiner* — Michael A Lyons
*Assistant Examiner* — Maurice Smith
(74) *Attorney, Agent, or Firm* — Foley & Lardner LLP (57) ABSTRACT

Systems and methods for detecting target chemicals are disclosed. A system includes a chemical sensor configured to filter light. The chemical sensor includes a referencing arm configured to output light at a first intensity level and a sensing arm sensitive to a target chemical. The sensing arm is configured to output light at a second intensity level. A difference between the first intensity level and the second intensity level indicates a presence of the target chemical.

20 Claims, 6 Drawing Sheets

(56) References Cited

U.S. PATENT DOCUMENTS

| | | |
|---|---|---|
| 7,697,796 B2 | 4/2010 | Kashyap et al. |
| 8,269,974 B2 | 9/2012 | Ash, III |
| 2002/0196993 A1 | 12/2002 | Schroeder |
| 2003/0161582 A1* | 8/2003 | Shigematsu ............ G02B 6/14 385/37 |
| 2003/0166294 A1* | 9/2003 | Kirby ................ G01N 21/3504 436/134 |
| 2007/0127019 A1* | 6/2007 | Zribi ........................ G01J 3/02 356/301 |
| 2010/0309454 A1* | 12/2010 | Zhang ...................... G01J 3/02 356/39 |
| 2012/0113422 A1* | 5/2012 | Kivioja ................ G01J 3/0205 356/328 |
| 2013/0301007 A1* | 11/2013 | Wolffsohn ............ A61B 3/032 351/239 |
| 2014/0200054 A1 | 7/2014 | Fraden |

OTHER PUBLICATIONS

International Search Report and Written Opinion in International Application No. PCT/IB2015/057302, mailed Dec. 3, 2015 (10 pages).

* cited by examiner

SYSTEMS FOR DETECTING TARGET CHEMICALS AND METHODS FOR THEIR PREPARATION AND USE

BACKGROUND

The following description is provided to assist the understanding of the reader. None of the information provided or references cited is admitted to be prior art.

Sensors can be used to detect various characteristics of an environment surrounding the sensor. For example, a chemical sensor can provide information related to the chemical composition of the environment surrounding an individual. The technology can have broad applications including environmental chemical monitoring, workplace safety monitoring, industrial process control, quality control, leak testing, biomedical monitoring, food and water testing, and drug detection.

SUMMARY

Systems for detecting target chemicals and methods for their preparation and use are provided herein. In one aspect, the system includes a chemical sensor configured to filter light. The chemical sensor includes at least one referencing arm configured to output light at a first intensity level and at least one sensing arm sensitive to a target chemical. The at least one sensing arm is configured to output light at a second intensity level. The at least one sensing arm and the at least one referencing arm further include at least one Bragg grating. The at least one Bragg grating is configured to reflect particular wavelengths of light and transmit non-reflective wavelengths. In an embodiment, the difference between the first intensity level and the second intensity level indicates a presence of the target chemical.

In another aspect, there is provided a method for detecting the presence of a target chemical. The method includes transmitting, by a light source, light through a chemical sensor. The chemical sensor includes a referencing arm and a sensing arm. The method further includes outputting, by the referencing arm, light at a first intensity level and outputting, by the sensing arm, light at a second intensity level. In an embodiment, the sensing arm is sensitive to a target chemical. The method further includes comparing, by an analyzing unit, the first intensity level and the second intensity level and detecting, by the analyzing unit, a presence of the target chemical based on a difference between the first intensity level and the second intensity level.

In a further aspect, there is provided a method making a chemical sensor for detecting target chemicals. The method includes creating a chemical sensor configured to filter light. The method further includes embedding a referencing arm into the chemical sensor. In an embodiment, the referencing arm is configured to output light at a first intensity level. The method further includes embedding a sensing arm into the chemical sensor. In an embodiment, the sensing arm is sensitive to a target chemical and the sensing arm is configured to output light at a second intensity level. A difference between the first intensity level and the second intensity level may indicate a presence of the target chemical.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are; therefore, not to be considered limiting of its scope, the disclosure will be described with additional specificity and detail through use of the accompanying drawings.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Disclosed herein are systems for detecting target chemicals and methods for their preparation and use. To detect the presence of a target chemical, a chemical sensor system is created. In an embodiment, the chemical sensor system is adaptable to mobile devices. The chemical sensor system includes a light filtering system using optical fiber sensors. Given their intrinsic capability to measure a multitude of parameters such as strain, temperature, pressure, chemical, and biological agents, and coupled with their flexibility of design to be used as single point or multi-point sensing arrays at low cost, fiber Bragg grating sensors may be used for as the optical fiber sensors.

As discussed above, in an embodiment, a chemical sensor system is created that is adaptable to mobile devices to detect the presence of at least one target chemical or agent. When adapting the chemical sensor for use with a mobile device, the chemical sensor has a simple design and reduced manufacturing costs since the chemical sensor can use features of the mobile device to operate. The minimal size of the chemical sensor according to the embodiments discussed herein allows for use of the chemical sensor in many different applications without adapting or altering the chemical sensor. The chemical sensor makes use of light filtering to detect the presence of chemicals and/or gases in the environment around the mobile device. In addition, the chemical sensor can generate alerts to notify an individual of the presence of the chemicals and/or gases. The technology has broad application including environmental chemical monitoring, workplace safety monitoring, industrial process control, quality control, leak testing, biomedical monitoring, food and water testing, and drug detection.

Figure 1:
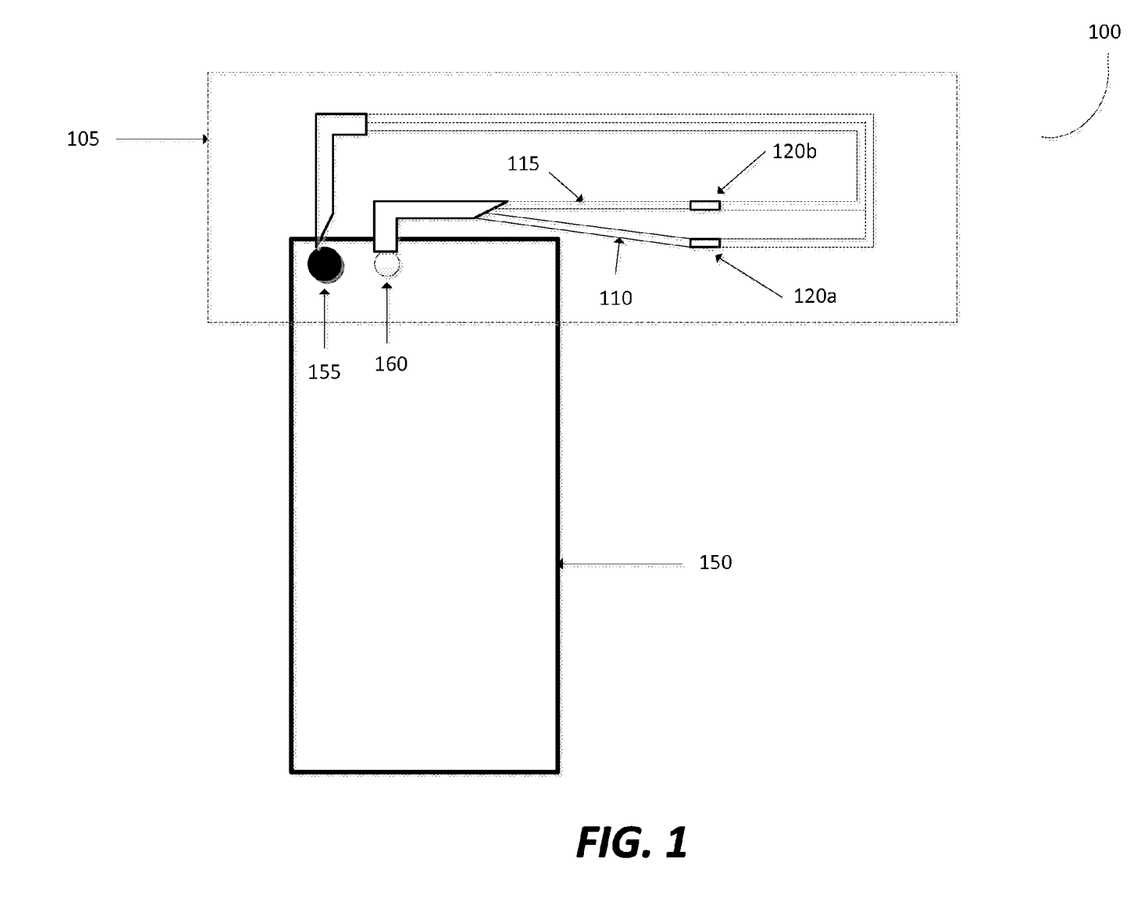
FIG. 1 depicts a system for detecting target chemicals in accordance with an illustrative embodiment.

FIG. 1 depicts a system 100 for detecting target chemicals in accordance with an illustrative embodiment. In an embodiment, the system 100 is a chemical sensor 105 configured to filter light. The chemical sensor 105 includes at least one referencing arm 110 and at least one sensing arm 115. The referencing arm 110 and the sensing arm 115 both include Bragg gratings 120a and 120b. In an embodiment, the chemical sensor 105 can be incorporated into a mobile device 150. In one embodiment, the chemical sensor 105 may be embedded into the mobile device 150. In other embodiments, the chemical sensor 105 can be a separate unit from the mobile device 150 and can be plugged into and/or otherwise coupled to the mobile device 150. For example, the chemical sensor 105 can be embedded into a mobile phone case as an accessory and attached to the mobile device 150 when the mobile phone case is coupled to the mobile device 150. The chemical sensor 105 may be plugged into the mobile device 150 via a connection to a universal serial bus (USB) port on the mobile device 150. In some embodiments, the chemical sensor 105 is wirelessly coupled to the mobile device 150.

In an embodiment, the chemical sensor 105 includes a bundle of optical fibers. The bundle of optical fibers may connect the chemical sensor 105 to at least one light source 160 at a first end and to at least one analyzing unit 155 at a second end. In an embodiment, the first end is a different end of the bundle of fibers than the second end. The optical fibers can be made up of at least one of glass, metal, or any type of polymeric material.

As mentioned above, the chemical sensor 105 includes the referencing arm 110 and the sensing arm 115. In an embodiment, the bundle of optical fibers may be split into the referencing arm 110 and the sensing arm 115. The referencing arm 110 may be a first segment of the bundle of optical fibers and the sensing arm 115 may be a second segment of the bundle of optical fibers. The referencing arm 110 and the sensing arm 115 can be made up of at least one of glass, metal, or any type of polymeric material. In some embodiments, the referencing arm 110 and the sensing arm 115 can be made up of the same material. In other embodiments, the referencing arm 110 and the sensing arm 115 are made up of different material.

In an embodiment, the various dimensions of the components are not limiting. For example, the length of the referencing arm 110 may be about 100 mm (millimeter) to about 300 mm, and the length of the sensing arm 115 may be about 100 mm to about 300 mm. In an embodiment, the outer diameter of the referencing arm 110 may be about 250 micrometers (μm) to about 500 μm, and the outer diameter of the sensing arm may be about 250 μm to about 500 μm. In alternative embodiments, the referring arm 1120 and the sensing arm 115 have any length and/or outer diameter that is suitable for a design need of the device. The referencing arm 110 and the sensing arm 115 may further include a fiber core, a cladding layer surrounding the fiber core, and a buffer layer surrounding the cladding layer. The buffer layer is the layer between the cladding layer and the outer jacket of the referencing arm 110 and the sensing arm 115. The layers of the referencing arm 110 and the sensing arm 115 will be described in greater detail with respect to FIGS. 2A and 2B below.

In an embodiment, each optical fiber includes at least one Bragg grating. For example, the referencing arm 110 has a Bragg grating 120a. The sensing arm 115 has a Bragg grating 120b. The Bragg gratings will be described in greater detail with respect to FIGS. 2A and 2B below.

In an embodiment, the referencing arm 110 is configured to output light at a first intensity level. The referencing arm 110 may be sensitive to temperature and pressure. In some embodiments, sensitive refers to an effect of environmental characteristics, for example temperature and/or pressure, on light passing through the fiber optic cable, for example the referencing arm 110 and the sensing arm 115. In one embodiment, the temperature and/or pressure can cause the intensity of light passing through the referencing arm 110 and/or the sensing arm 115 to be reduced as it passes through the fiber optic cable. The temperature refers to a temperature of the environment around the chemical sensor 105. The pressure refers to an atmospheric pressure of the environment around the chemical sensor 105. The sensing arm 115 may be sensitive to temperature, pressure, and a target chemical.

In an embodiment, the sensing arm 115 is sensitive to a target chemical and configured to output light at a second intensity level. The sensing arm 115 may include a coating configured to bind with a molecule of the target chemical. The coating may include an activated carbon, a Thiol group compound, or a metal-organic framework compound. In one embodiment, the sensing arm 115 is coated with a heme-based ligand (iron) to detect carbon monoxide. In other embodiments, the sensing arm 115 is coated with a copper based ligand to detect nitrogen oxide.

In some embodiments, the sensing arm 115 is coated with more than one material and can bind with more than one type of target chemical. The target chemical may be a volatile organic compound (VOC), for example and without limitation, ammonia, formaldehyde, ethyl acetate, glycol ethers, acetone, chlorofluorocarbons, benzene, styrene, limonene, gasoline, gasoline exhausts, methylene chloride, perchloroethylene, and methyl tertiary butyl ether (MTBE). In other embodiments, the target chemical may be a pollutant, for example and without limitation, carbon monoxide (CO), nitrogen oxide ($NO_x$), and radon. The target chemical may be present in ambient air in the environment around the chemical sensor 105. The coated sensing arm 115 can detect the presence of the target chemical as discussed below.

In an embodiment, the surface of the sensing arm 115 includes at least one coating configured to bind with a molecule of the target chemical. The presence of the target chemical can change a refractive index of the sensing arm 115. In one embodiment, the surface of the sensing arm 115 is coated with a ligand that is capable of binding specifically with the target chemical. If the target chemical is present in the environment surrounding the chemical sensor 105, the ligand binds with the molecules of the target chemical and changes a refractive index of the sensing arm 115. The refractive index of the optical fiber describes how light or radiation propagates through that medium. The refractive index determines how much light is bent or refracted when entering the material. In an embodiment, the chemical sensor 105 detects the change in the refractive index by measuring the intensity of light at the output of the sensing arm 115. If the intensity of light has been reduced, this reduction may indicate the presence of the target chemical.

In an embodiment, the values of the intensity of light outputted by each of the referencing arm 110 and the sensing arm 115 are compared other values to detect the presence of target chemicals. The detected values may be compared to an initial value entering the referencing arm 110 and/or the sensing arm 115. The initial value refers to the initial intensity of light output by the light source 160 into the referencing arm 110 and the sensing arm 115. In other embodiments, the detected values may be measured against pre-determined values, for example, threshold values. In some embodiments, a reduction in the intensity of light through at least one of the referencing arm 110 and sensing arm 115 may indicate the presence of the target value and/or the type of target chemical. In other embodiments, an increase in the intensity of light through at least one of the referencing arm 110 and the sensing arm 115 may indicate the presence of the target value and/or the type of target chemical. In some embodiments, a measurement below a threshold value may indicate the presence of the target value and/or the type of target chemical. In other embodiments, a measurement above a threshold value may indicate the presence of the target value and/or the type of target chemical. For example, in one embodiment, a threshold value of 50 parts per million per hour (ppm/hour) for carbon monoxide is used. A measurement greater than 50 ppm/hour of carbon monoxide indicates an unsafe environment.

In other embodiments, the surface of the sensing arm includes a coating configured to fluoresce in the presence of the target chemical. The sensing arm 115 may be modified with a molecule that is capable of florescence in the presence of the target chemical. If the target chemical is present in the environment surrounding the chemical sensor 105, the molecule binds with the molecules of the target chemical and causes the surface of the sensing arm 115 to emit light via fluorescence. In some embodiments, the chemical sensor 105 may include an ultraviolet (UV) light to detect the fluorescence.

In an embodiment, the light source 160 is configured to transmit light through the referencing arm 110 and the sensing arm 115. In one embodiment, the light source 160 is a flash of a camera of the mobile device 150. In other embodiments, the light source is an infrared light-emitting diode. The chemical sensor 105 may be connected to the flash of the mobile device's camera at the first end, e.g., at the light source 160. The light emitted by the flash can be outputted by the referencing arm 110 and the sensing arm 115 to the analyzing unit 155. In other embodiments, the light source 160 can be a separate unit coupled to the first end of the chemical sensor 105. For example, the light source 160 can be embedded into a mobile phone case as a separate unit and be coupled to the first end of the chemical sensor 105.

In an embodiment, the analyzing unit 155 is configured to detect the presence of the target chemical in response to comparing the first intensity level output by the referencing arm 110 to the second intensity level output by the sensing arm 115. The analyzing unit 155 may include at least one charge-coupled device sensor in the camera of the mobile device 150. The analyzing unit 155 is configured to read the light intensity change exiting the second end of the optical fibers and provide a reading of the light intensity. Differences between the intensity level of light outputted by different optical fibers of the chemical sensor 105 may indicate the presence of the target chemical in the environment around the chemical sensor 105. In some embodiments, the analyzing unit includes the camera unit of a mobile device 150. For example, in one embodiment, the second end of the referencing arm 110 and the sensing arm 115 are coupled to the lens of the camera unit of the mobile device 150.

In other embodiments, the analyzing unit 155 may be at least one micro optical ring resonator. The micro optical ring resonator may include a set of waveguides, in which at least one waveguide is a closed loop, coupled to the light input and the light output. When light of the resonant wavelength is passed through the loop from the input waveguide, it builds up in intensity over multiple round-trips due to constructive interference. Because only a select few wavelengths will be at resonance within the loop, the optical ring resonator functions as a filter. In an embodiment, it is possible to create high-order optical filters by cascading many optical ring resonators in series. This results in a small-size, low-loss, fiber network-integrating optical filter that can greatly reduce background noise for Raman signals.

In an embodiment, chemical sensor 105 may include at least one heating mechanism configured to maintain a substantially constant temperature in the chemical sensor 105. In one embodiment, the micro optical ring resonator is maintained at a substantially constant temperature using the heating mechanism. The heating mechanism may reduce or eliminate interference resulting from temperature variations. In some embodiments, the heating mechanism may include thermoelectric heating to control and/or adjust the temperature inside the chemical sensor 105. For example, in one embodiment, a thermometer monitoring the temperature of the micro optical ring resonator is connected to a switch that directs the flow of electricity in the vicinity of the micro optical ring resonator. In electronic form, a band-gap temperature sensor involving several pn junctions can sense the temperature around the micro optical ring resonator and adjust the current level used to heat the region around the resonator using a servo-loop mechanism.

In other embodiments, the chemical sensor 105 does not include a heating mechanism and the referencing arm is used to account for fluctuations in transmission due to temperature variation. The referencing arm and the sensing arm are effected in the same way by the temperature variations and any changes in intensity of light transmitted through the referencing arm and sensing arm will be the same, mitigating any effects of temperature variation on the chemical sensor 105 detection readings.

In an embodiment, the chemical sensor 105 includes at least one USB port. The chemical sensor 105 can connect to and communicate with a mobile device via a port on the mobile device 150, for example, the USB port. The chemical sensor 105 communicates and transmits data to the mobile device through the USB port. In an embodiment, the chemical sensor 105 is powered by the mobile device 150 through the connection established by the USB port. For example, the chemical sensor 105 can function with any device capable of powered USB interfacing through the USB port. Example devices include at least one of a laptop, cell phone, tablet computer, or any type of handheld computing device. In some embodiments, the chemical sensor 105 is coupled to and communicate with the mobile device 150 though any port and/or interface of the mobile device 150. In other embodiments, the chemical sensor 105 is battery powered and the port may be omitted. In some embodiments, the chemical sensor 105 may be communicatively coupled to the mobile device 150 and may communicate wirelessly with the mobile device 150 via Bluetooth or WiFi connection.

Figure 2A:
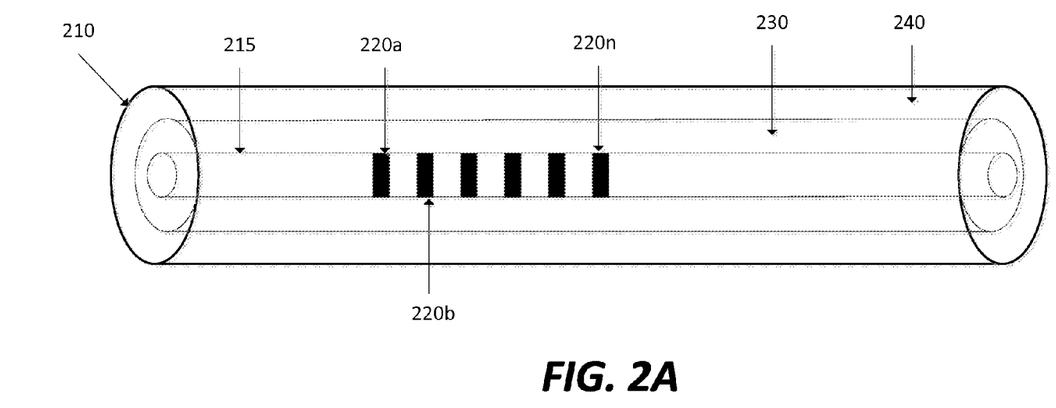
FIG. 2A depicts an optical fiber in accordance with a first illustrative embodiment.

FIG. 2A depicts an optical fiber 210 in accordance with a first illustrative embodiment. The optical fiber 210 includes a fiber core 215, Bragg gratings 220a-n, a cladding layer 230, and a buffer layer 240. The optical fiber 210 may be one optical fiber in a bundle of optical fibers making up the chemical sensor 105 described above with respect to FIG. 1. In an embodiment, a first end of the optical fiber 210 is connected to a light source and a second end of the optical fiber 210 is connected to an analyzing unit. The optical fiber 210 transmits light received from the light source to the analyzing unit. The intensity of light received at the analyzing unit depends on the characteristics of the optical fiber 210 and the characteristics of the environment around the optical fiber 210.

In an embodiment, the optical fiber 210 includes a fiber core 215. The fiber core 215 may be a cylinder that runs along the optical fiber's length. The fiber core 215 may include a glass, plastic material, or polymeric material. In some embodiments, the fiber core 215 is made up of at least one of silica, fluoride glass, phosphate glass, or chalcogenide glass. In other embodiments, the fiber core 215 may include helium hydride ion ($HeH^+$), polyethylene, polyvinyl chloride (PVC), or polyurethane. The outer diameter of the fiber core 215 may be up to about 100 µm. In one embodiment, the outer diameter of the fiber core 215 is about 8 µm. In alternative embodiments, the fiber core 215 has any length and/or outer diameter that is suitable for a design need of the device. In an embodiment, the cross-section of the fiber core 215 is circular and/or cylindrical.

The fiber core 215 is surrounded by a medium with a lower index of refraction than the fiber core 215. In an embodiment, the medium is the cladding layer 230. In an embodiment, the cladding layer 230 may include a different glass, plastic, or polymeric material than that of the fiber core 215. In some embodiments, the outer diameter of the cladding layer 230 may be about 50 µm to about 250 µm. In an embodiment, the cladding layer 230 has an outer diameter of about 125 µm. In alternative embodiments, the cladding layer 230 has an outer diameter of any size that is suitable for a design need of the device. Light is maintained in the fiber core 215 by total internal reflection. Light traveling through the fiber core 215 may reflect from the fiber core-cladding boundary due to total internal reflection when the angle between the light and the fiber core-cladding boundary is less than the critical angle. As a result, the fiber core 215 acts as a waveguide and transmits all rays of light that enter the fiber core 215 with a sufficiently small angle, also referred to as a limiting angle, to the fiber core's 215 axis. In some embodiments, the limiting angle is called the acceptance angle and the rays of light that are confined by the core-cladding boundary are called guided rays. The limiting angle is the smallest angle of incidence at which a ray of light passing from one medium to another less refractive medium can be totally reflected from the boundary between the two.

In an embodiment, the cladding layer 230 is surrounded and/or coated with a buffer layer 240. The buffer layer 240 protects the cladding layer 230 from moisture and physical damage. In some embodiments, the buffer layer 240 is a resin material, for example, a UV-cured urethane acrylate composite material. In some embodiments, the outer diameter of the buffer layer 240 may be about 125 µm to about 400 µm. In an embodiment, the outer diameter of the buffer layer 240 is about 250 µm. In alternative embodiments, the buffer layer 240 has an outer diameter of any size that is suitable for a design need of the device. The optical fiber includes a jacket 250 that surrounds the buffer layer 240. In an embodiment, the jacket 250 is a glass material. In some embodiments, the outer diameter of the jacket 250 may be between about 250 µm to about 500 µm. In an embodiment, the jacket 250 has an outer diameter of about 400 µm. In alternative embodiments, the jacket 250 has an outer diameter of any size that is suitable for a design need of the device. The dimensions of the different layers of the optical fiber 210 (e.g., fiber core, cladding layer, buffer layer, jacket) and the dimensions of the optical fiber 210 may be selected dependent upon the strength of detection desired, the wavelength, and the modality of the evanescent wave for detection.

In an embodiment, the optical fiber 210 includes Bragg gratings 220$a$-$n$ configured to reflect particular wavelengths of light and transmit non-reflective wavelengths. The Bragg gratings 220$a$-$n$ are fiber Bragg gratings constructed in a segment of the optical fiber 210, for example, the fiber core 215, the cladding layer 230, the buffer layer 240, or the jacket 250. In an embodiment, the Bragg gratings 200$a$-$n$ are exposed to the environment around the chemical sensor. The fiber Bragg gratings can be used as an inline optical filter to block certain wavelengths or as a wavelength-specific reflector. Each Bragg grating 220$a$-$n$ may have a period of a few hundred nanometers. The periodicity of the grating depends on the wavelengths used by the sensor. In some embodiments, long period Bragg gratings can be used and have periods in the order of hundreds of microns.

Figure 2B:
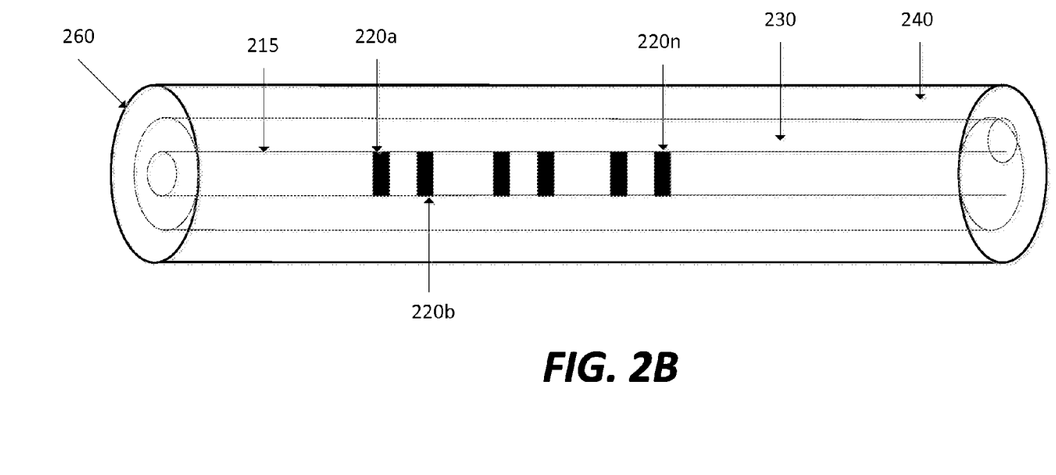
FIG. 2B depicts an optical fiber in accordance with a second illustrative embodiment.

The characteristics and structure of the Bragg gratings 220$a$-$n$, including a grating period, can be varied to control the refractive index of the optical fiber 210. The grating period can be uniform or graded, and either localized or distributed in a superstructure. FIG. 2A depicts uniform fiber Bragg gratings 220$a$-$n$ in the fiber core 215. In contrast, FIG. 2B depicts a set of superstructure fiber Bragg gratings 220$a$-$n$ in the fiber core 215 of an optical fiber 210 in accordance with a second illustrative embodiment. The optical fiber 210 of FIG. 2A and the optical fiber 260 of FIG. 2B may be similar except for the difference in the structure of the respective fiber Bragg gratings 220$a$-$n$. The difference in the structure of the Bragg gratings 220$a$-$n$ results in a change in the refractive index of the respective optical fibers.

The structure of the Bragg grating 220$a$-$n$ can be at least one of uniform positive-only index change, Gaussian apodized, raised-cosine apodized, chirped, tilted, discrete phase shift, or superstructure. In an embodiment, there are two quantities that control the properties of the fiber Bragg grating, that is, the grating length and grating strength. However, there are three properties that need to be controlled, that is, the reflectivity, the bandwidth, and the side-lobe strength. The various structures of the Bragg gratings 220$a$-$n$ control these properties. The grating length can be used to set the peak reflectivity and the grating strength can be used to set the bandwidth. This leaves the side-lobe strength to be controlled. The side-lobes can be removed by using apodized gratings. In apodized gratings, the strength of the index modulation is smoothly ramped up and down along the grating to suppress or remove the side-lobes from the reflection spectrum of the Bragg gratings 220$a$-$n$.

In an embodiment, each of the Bragg gratings 220$a$-$n$ may have a different periodicity along the fiber core 215. The periodicity of each Bragg grating 220$a$-$n$ may be tailored to a specific target chemical. An optical fiber 210 with multiple Bragg gratings 220$a$-$n$ having different periodicities can detect different target chemicals with the same chemical sensor. In an embodiment, a sensing arm includes a first portion with a first Bragg grating 220$a$ and a second portion with a second Bragg grating 220$b$.

The first Bragg grating 220$a$ may be a different length than the second Bragg grating 220$b$. In some embodiments, the first Bragg grating 220$a$ may be sensitive to a different chemical target than the second Bragg grating 220$b$. In one embodiment, the first Bragg grating 220$a$ of the first portion has a long period Bragg grating that is sensitive to a first target chemical. The second Bragg grating 220$b$ of the second portion may have a short period Bragg grating that is sensitive to a second target chemical. The application of Bragg gratings 220$a$-$n$ can effectively reduce the intense Rayleigh scattered laser light that usually accompanies the typically relatively weak Raman scattering, thus removing the main difficulty of Raman's spectroscopy.

Figure 3:
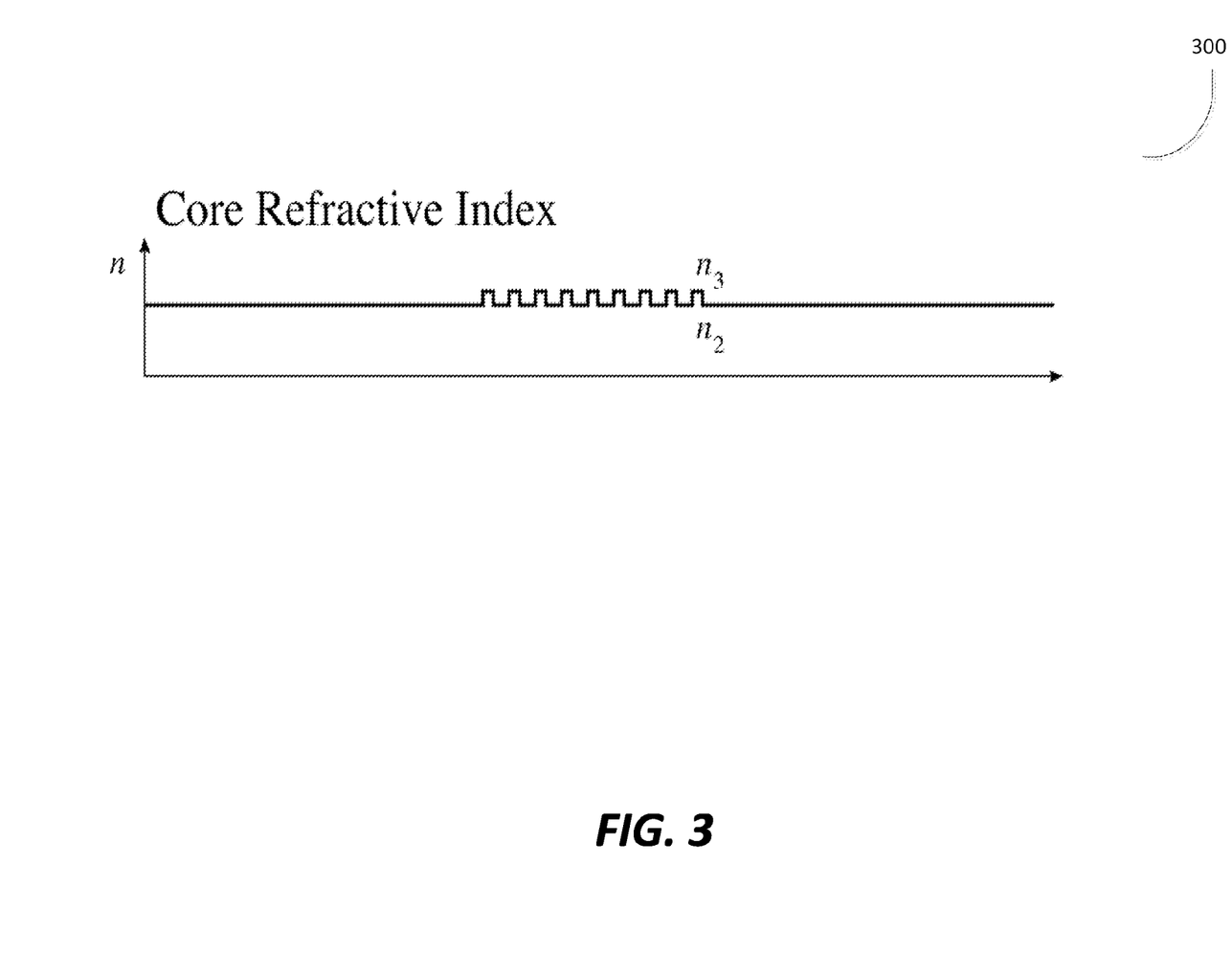
FIG. 3 depicts a refractive index profile of an optical fiber in accordance with an illustrative embodiment.

FIG. 3 depicts a refractive index profile 300 of an optical fiber in accordance with an illustrative embodiment. In more detail, FIG. 3 depicts a uniform refractive index profile 300 corresponding to the optical fiber 210 described above with respect to FIG. 2A. The refractive index profile is the distribution of refractive indices of materials within an optical fiber and illustrates how light is reflected by the Bragg gratings 220a-n. A refractive index indicates the way in which light will travel through a particular substance in relation to how it travels through a vacuum. When light moves through a medium of a given refractive index ($n_2$) into a second medium with a different refractive index ($n_3$), both reflection and refraction of the light can occur. The refractive index has two primary characteristics, the refractive index profile and the offset. The refractive index profile can be uniform or apodized, and the refractive index offset is positive or zero.

Figures 4A, 4B:
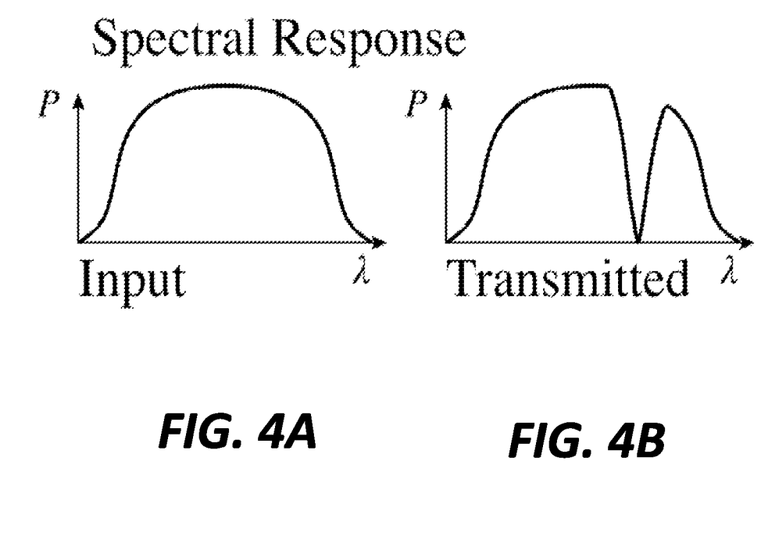
FIG. 4A depicts a graph of inputted light through an optical fiber in accordance with an illustrative embodiment.
FIG. 4B depicts a graph of refracted light through an optical fiber in accordance with an illustrative embodiment.
Figure 4C:
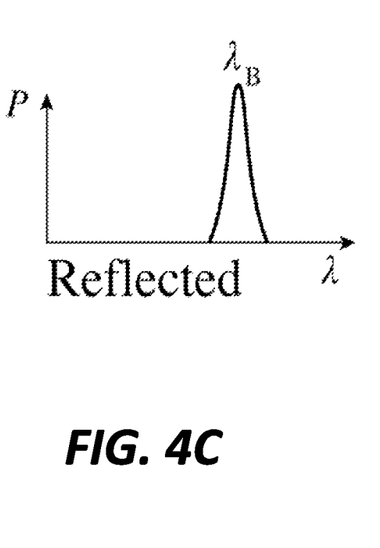
FIG. 4C depicts a graph of reflected light in an optical fiber in accordance with an illustrative embodiment.

FIGS. 4A-4C depict graphs of a spectral response of an optical fiber in accordance with an illustrative embodiment. In each of the figures, the power (P) is graphed versus the wavelength (A). The optical fiber includes fiber Bragg gratings causing light traveling through the optical fiber to both reflect and refract (transmit) in the optical fiber. The operation of a fiber Bragg grating is also referred to as a Fresnel reflection, which describes the behavior of light when moving between media of different refractive indices. In the optical fiber, the refractive index will vary over the length of the optical fiber depending on the characteristics of the optical fiber, for example, if the optical fiber includes fiber Bragg gratings.

FIG. 4A depicts a graph of the inputted light through a fiber core. For example, the light inputted by the light source to a referencing arm and a sensing arm of a chemical sensor. FIG. 4B depicts a graph of the refracted (transmitted) light through the optical fiber of a chemical sensor as it corresponds to the inputted light from FIG. 4A. FIG. 4C depicts a graph of the reflected light in the optical fiber as it corresponds to the inputted light from FIG. 4A. The reflected light is indicated at the reflected wavelength ($\lambda_b$). The reflected light wavelength may also be referred to as the Bragg wavelength. The reflected wavelength corresponds to the portion of light not transmitted through the optical fiber to an analyzing unit of the chemical sensor and reducing the intensity of light received at the analyzing unit. The reflected wavelength can be controlled by the use of fiber Bragg gratings.

Figure 5:
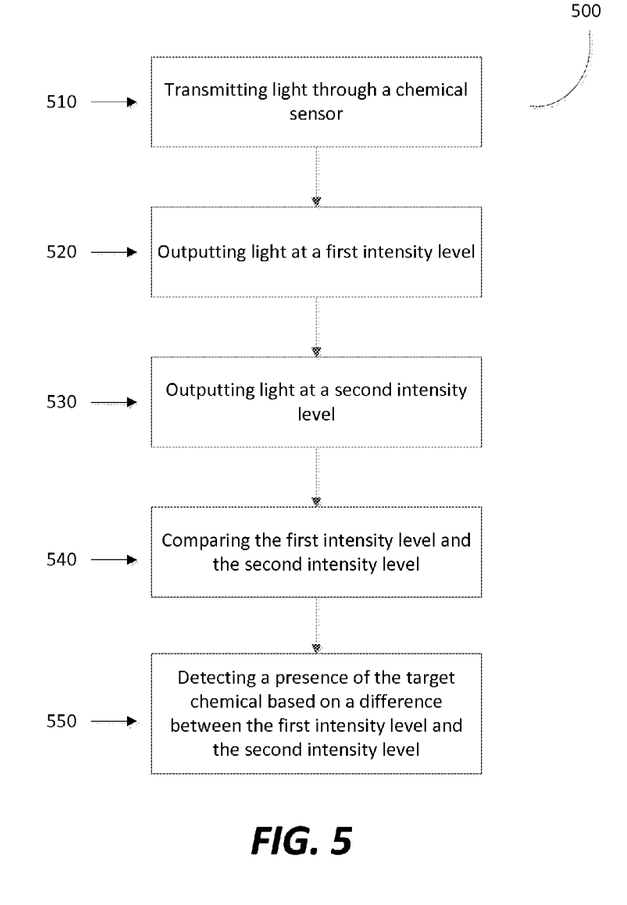
FIG. 5 depicts a flow diagram of a method for detecting a target chemical in accordance with an illustrative embodiment.

FIG. 5 depicts a flow diagram of a method for detecting a target chemical in accordance with an illustrative embodiment. In a brief overview, the method 500 includes transmitting light through a chemical sensor (510). The method further includes outputting light at a first intensity level (520) and outputting light at a second intensity level (530). The method further includes comparing the first intensity level and the second intensity level (540) and detecting a presence of the target chemical based on a difference between the first intensity level and the second intensity level (550).

As indicated above, the method includes transmitting, by a light source, light through a chemical sensor (510). The chemical sensor includes a referencing arm and a sensing arm. The light source is connected to a first end of the referencing arm and a first end of the sensing arm and can transmit light through both the referencing arm and the sensing arm. In an embodiment, initially the light enters both the referencing arm and the sensing arm at the same intensity level. For example, the referencing arm and the sensing arm may be both connected to a flash of a camera unit of a mobile device and receive light from the same light source.

In an embodiment, the sensing arm and the referencing arm further include a Bragg grating to reflect particular wavelengths of light and transmit the remaining wavelengths of light. In some embodiments, the Bragg grating effects light transmitted through the referencing arm and the sensing arm. The sensing arm may include a first portion with a first Bragg grating and a second portion with a second Bragg grating. The first Bragg grating may have different characteristics than the second Bragg grating. In one embodiment, the first Bragg grating may be sensitive to a different chemical target than the second Bragg grating. In some embodiments, the first Bragg grating is a different length than the second Bragg grating.

The characteristics of a Bragg grating on the referencing arm may be different than the characteristics of a Bragg grating on the sensing arm. In an embodiment, the Bragg grating of the referencing arm is not sensitive to a target chemical and the Bragg grating of the sensing arm is sensitive to a target chemical. In one embodiment, the Bragg grating of the referencing arm is not coated with a material to attract and/or bind with molecules of a target chemical to detect the presence of the target chemical.

The method further includes outputting, by the referencing arm, light at a first intensity level (520). In an embodiment, the light inputted by the light source at the first end of the referencing arm may traverse the referencing arm and reach the second end of the referencing arm at the first intensity level. The first intensity level may be different than the intensity level of the light output by the light source initially. The referencing arm may be sensitive to temperature and pressure of an environment to which the chemical sensor is exposed. In some embodiments, a change in intensity level of the light traversing the referencing arm is caused by the temperature and pressure of the environment to which the chemical sensor is exposed. In an embodiment, the change in intensity level of the light traversing the referencing arm is effected by the characteristics of the referencing arm (for example, dimensions, material type) and characteristics of the environment around the referencing arm.

The method further includes outputting, by the sensing arm, light at a second intensity level (530). In an embodiment, the light inputted by the light source at the first end of the sensing arm may traverse the sensing arm and reach the second end of the sensing arm at the second intensity level. The second intensity level may be different than the intensity level of the light output by the light source initially. The sensing can be sensitive to a target chemical. In an embodiment, the sensing arm is sensitive to temperature, pressure, and the target chemical of an environment to which the chemical sensor is exposed. In an embodiment, the change in intensity level of the light traversing the sensing arm is effected by the characteristics of the sensing arm (for example, dimensions, material type) and characteristics of the environment around the sensing arm.

The method further includes binding, by a surface of the sensing arm, to a molecule of the target chemical. The surface of the sensing arm can be coated with a material to attract and/or bind with molecules of a target chemical to detect the presence of the target chemical. When the target chemical is in the environment around the chemical sensor, the molecules of the target chemical can bind with the surface of the sensing arm. The presence of the target chemical can change a refractive index of the sensing arm. When the molecules of the target chemical bind with the surface of the sensing arm, the characteristics of the surface arm can change. This change can result in a change in the refractive index and the way in which the sensing arm transmits light. This change in refractive index can then be detected to indicate the presence of the target chemical in the environment around the chemical sensor. If no change is detected, this indicates that the target chemical is not present in the environment around the chemical sensor.

In some embodiments, the method includes applying at least one coating to a surface of the sensing arm. The coating can have the property of fluorescence and be configured to emit a light in the presence of the target chemical. When the target chemical is present in the environment around the chemical sensor, the coating on the surface of the sensing arm can emit a light in response. In some embodiments, the fluorescence on the surface of the sensing arm can be detected with a UV light. In an embodiment, the target chemical includes at least one of a volatile organic compound, a pollutant, or radon.

The method further includes comparing, by an analyzing unit, the first intensity level and the second intensity level (540). In an embodiment, the second end of the referencing arm and the second end of the sensing arm are connected to the analyzing unit. The analyzing unit is configured to receive light outputted by both the referencing arm and the sensing arm. In an embodiment, the analyzing unit measures the light intensity output at the second end of the referencing arm and a light intensity output at the second end of the sensing arm. The analyzing unit then compares the light intensity from the referencing arm to the sensing arm. In some embodiments, the analyzing unit compares the detected light intensity from the sensing arm and the referencing arm to values stored in a database or memory. The stored values may include predicted values or threshold values used to determine if a target chemical is present. The method can further include analyzing known target chemical samples to prepare a calibration curve prior to or after analyzing an environment.

The method further includes detecting, by the analyzing unit, a presence of the target chemical based on a difference between the first intensity level and the second intensity level (550). In an embodiment, a difference in light intensity received from the sensing arm and the referencing arm indicates the presence of the target chemical. The light intensity from the referencing arm can be the different than the light intensity from the sensing arm. In response to detecting the presence of the target chemical, the chemical sensor may generate an alert to a user of the chemical sensor to notify them of the target chemical.

In an embodiment, the chemical sensor is embedded into a mobile device. The chemical sensor may generate an alert on a mobile device to which it is communicatively coupled. The mobile device can generate an alert to the user of the mobile device. The alert may include at least one of or a combination of tactile, visual, or auditory signals. In some embodiments, the chemical sensor transmits an alert to multiple computing devices in response to detecting the target chemical.

In other embodiments, the light intensity from both the referencing arm and the sensing arm is the same. If the analyzing unit does not detect a difference from the light intensity received from the referencing arm and the light intensity received from the sensing arm, the environment around the chemical sensor does not contain the target chemical. The chemical sensor may generate a notification to a user of the chemical sensor that the environment lacks the target chemical. In some embodiments, the target chemical is undesired, and in other embodiments the target chemical is desired.

In an embodiment, the method further includes heating, by a heating mechanism, the chemical sensor to maintain a substantially constant temperature in the chemical sensor. The chemical sensor may include a heating mechanism to maintain a constant temperature in the chemical sensor. In an embodiment, the heating mechanism is used to maintain a micro optical ring resonator at a constant temperature. The heating mechanism may reduce or eliminate the interference of temperature variation in the various environments the chemical sensor is exposed. In some embodiments, a cooling mechanism is used to maintain a substantially constant temperature in the chemical sensor. In an embodiment, a thermometer is used to monitor the temperature in the chemical sensor. In response to the temperature going above or below a threshold value, the chemical sensor powers on or off the heating mechanism or the cooling mechanism. A switch can be coupled to the thermometer and in response to detecting a temperature outside of a pre-determined range, the switch can power on or off the heating mechanism or the cooling mechanism. In some embodiments, the switch is used to transition from heating and cooling the chemical sensor to maintain the chemical sensor at a desired temperature.

Figure 6:
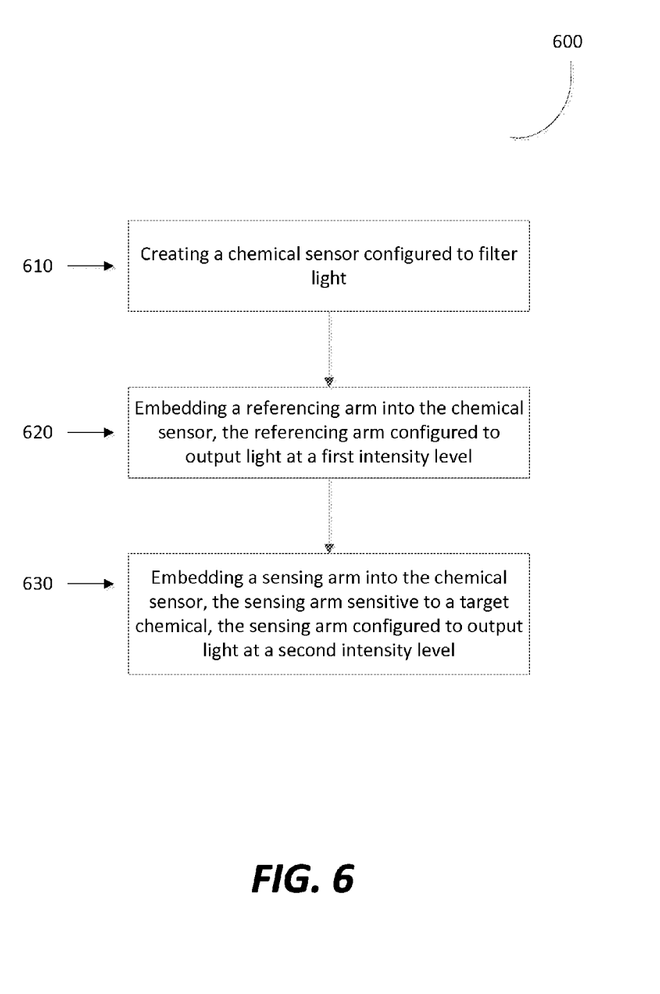
FIG. 6 depicts a flow diagram of a method for creating a chemical sensor in accordance with an illustrative embodiment.

FIG. 6 depicts a flow diagram of a method 600 for creating a chemical sensor. In a brief overview, the method 600 includes creating a chemical sensor to filter light (610). The method further includes embedding a referencing arm into the chemical sensor (620) and embedding a sensing arm into the chemical sensor (630).

As indicated above, the method 600 includes creating a chemical sensor configured to filter light (610). The chemical sensor may include a bundle of optical fibers. A first end of the bundle of optical fibers is coupled to a light source. In an embodiment, the first end of the bundle of optical fibers is coupled to the flash of a camera of a mobile device. The bundle of optical fibers can be split into two portions, a referencing arm and a sensing arm.

The method further includes embedding a referencing arm into the chemical sensor (620). The referencing arm may be a first portion of the bundle of optical fibers. In an embodiment, the referencing arm is embedded into the chemical sensor by adding at least one optical fiber. A first end of the referencing arm is coupled to the light source. The referencing arm may be configured to output light at a first intensity level at a second end of the referencing arm. The second end of the referencing arm is coupled to an analyzing unit.

The method further includes embedding a sensing arm into the chemical sensor (630). The sensing arm may be a second portion of the bundle of optical fibers. In an embodiment, the sensing arm is embedded into the chemical sensor by adding at least one optical fiber. A first end of the sensing arm is coupled to the light source. The sensing arm may be configured to output light at a second intensity level at a second end. The second end of the sensing arm is coupled to an analyzing unit. The analyzing unit is configured to detect the presence of the target chemical in response to comparing the first intensity level output by the referencing arm to the second intensity level output by the sensing arm.

In an embodiment, the sensing arm is sensitive to a target chemical. The method further includes coating a surface of the sensing arm. The coating can be configured to bind with a molecule of the target chemical. The presence of the target chemical can change a refractive index of the sensing arm in response to the coating of the sensing arm binding with the molecule of the target chemical. In other embodiments, the surface of the sensing arm is coated and the coating is configured to fluoresce in the presence of the target chemical.

In an embodiment, the sensing arm and the referencing arm further include a Bragg grating configured to reflect particular wavelengths of light and transmit non-reflective wavelengths. The Bragg gratings 220a-n are created by inscribing and/or writing systematic variations of refractive index into the fiber core of an optical fiber using a UV source, such as a UV laser. The systematic variations may be periodic or aperiodic variations. The process of either interference or masking can be used to create the Bragg gratings in each of the sensing arm and the referencing arm.

Interference refers to a process in which a UV laser is split into two beams to interfere with each other creating a periodic intensity distribution along an interference pattern. The refractive index of the photosensitive fiber core changes according to the intensity of light that it is exposed to. Masking refers to a process in which a mask, also referred to as a photomask, is placed between the UV light source and the photosensitive fiber core. The shadow of the mask determines the grating structure based on the transmitted intensity of the light striking the fiber core. The method used to create the Bragg grating depends on the type of grating to be manufactured. The amount of change in the refractive index of an optical fiber depends on the intensity and duration of the exposure as well as the photosensitivity of the fiber.

In an embodiment, the method includes coupling a heating mechanism to the chemical sensor. The heating mechanism is configured to maintain a constant temperature in the chemical sensor. In some embodiments, the method includes coupling a cooling mechanism to the chemical sensor. In an embodiment, a thermometer is embedded into the chemical sensor to monitor the temperature in the chemical sensor. In response to the temperature going above or below a threshold value, the chemical sensor powers on or off the heating mechanism or the cooling mechanism. A switch can be coupled to the thermometer and in response to detecting a temperature outside of a pre-determined range, the switch can power on or off the heating mechanism or the cooling mechanism. In some embodiments, the switch is used to transition from heating and cooling the chemical sensor to maintain the chemical sensor at a desired temperature.

In an embodiment, the method includes embedding the chemical sensor into a mobile phone case. The mobile phone case does not have to contain other electronics or components, therefore, the chemical sensor does not have to be designed around additional components as it would if it was embedded in an existing electronic device. Additionally, the mobile phone case provides more space for optical fibers to be used in detecting various target chemicals than if the chemical sensor was embedded in another device.

The referencing arm and the sensing arm can be embedded into the mobile phone case. In some embodiments, a light source is embedded into the mobile phone case and is coupled to a first end of the referencing arm and the sensing arm. In other embodiments, the chemical sensor is aligned in the mobile phone case such that when the mobile phone case is coupled to a mobile device, the chemical sensor is configured to receive light from a light source on the mobile device. An analyzing unit can be embedded into the mobile device. The analyzing unit is coupled to a second end of the referencing arm and the sensing arm of the chemical sensor. In other embodiments, the chemical sensor is aligned in the mobile phone case such that when the mobile phone case is coupled to a mobile device, the chemical sensor is configured to output light to an analyzing unit on the mobile device.

In an embodiment, the chemical sensor is a component of a mobile device. The light source may be the flash of the mobile device's camera. The referencing arm and the sensing arm can be coupled to the flash of the camera. The flash can transmit light through the referencing arm and the sensing arm. The analyzing unit may be a component of the mobile device as well. In one embodiment, the analyzing unit is the camera on the mobile device. The referencing arm and the sensing arm can be coupled to the analyzing unit. In such an embodiment, the chemical sensor, light source, and the analyzing unit are all components of the mobile device.

EXAMPLES

Example 1

Chemical Sensor Embedded into a Mobile Device

In a first example, a chemical sensor is embedded into a mobile device. The embedded chemical sensor is powered by the mobile device. The chemical sensor includes a bundle of optical fibers split into two portions. The first portion is a referencing arm and the second portion is a sensing arm. The referencing arm is sensitive to the temperature and pressure of the environment around the mobile device. The sensing arm is sensitive to the temperature and the pressure of the environment around the mobile device, as well as target chemical carbon monoxide. The chemical sensor is used to detect the presence of this target chemical.

The chemical sensor filters light received from the flash of the camera unit of the mobile device and outputs the light at an analyzing unit embedded in the mobile device. A first end of the referencing arm and the sensing arm are coupled to the light source and receive light at the same intensity level. A second end of the referencing arm and the sensing arm output light at the analyzing unit. The intensity of the light output at the analyzing unit can vary from the referencing arm and the sensing arm.

The referencing arm and the sensing arm both include Bragg gratings in their respective fiber core. The Bragg gratings have a uniform positive-only index change structure. The sensing arm is coated with a heme-based ligand (iron), specifically selected based on its ability to bond with a molecule of carbon monoxide. The surface of the chemically coated sensing arm will bond with molecules of carbon monoxide if carbon monoxide is present in the environment the mobile device.

An individual carries the mobile device into a basement of a house to test for chemicals and/or gases present. The basement contains levels of carbon monoxide of which the individual is previously unaware. When the individual enters the basement, the molecules of the carbon monoxide bond with the surface of the coated sensing arm of the chemical sensor embedded into the mobile device. The bonding of molecules of carbon monoxide with the surface of the sensing arm results in a change in the intensity of the light transmitted through the sensing arm. The referencing arm is not coated and does not bond with molecules of the carbon monoxide and the intensity of light transmitted through the referencing arm does not change when the individual enters the basement.

The analyzing unit in the chemical sensor detects a difference in the intensity of light output by the sensing arm as compared to the referencing arm. The analyzing unit determines that the difference falls above a threshold of 50 ppm/hour value and determines that the target chemical, carbon monoxide, is present and at an unsafe level in the environment around the mobile device and the individual. In response to detecting the carbon monoxide, the chemical sensor communicates with a microprocessor of the mobile device. The chemical sensor instructs the mobile device to vibrate and flash a warning on a user interface of the mobile device to warn the individual of the presence of the carbon monoxide.

Example 2

Chemical Sensor Embedded into a Mobile Device Case

A chemical sensor is embedded into a mobile phone case. The mobile phone case is coupled to a mobile device. The mobile phone case includes interconnects to connect the chemical sensor to components of the mobile device. The embedded chemical sensor is powered by the mobile device through a USB port and communicates with the mobile device through the USB port. The chemical sensor includes a bundle of optical fibers split into two portions. The first portion is a referencing arm and the second portion is a sensing arm. The referencing arm is sensitive to the temperature and pressure of the environment around the mobile device. The sensing arm is sensitive to the temperature and the pressure of the environment around the mobile device, as well as a target chemical. The chemical sensor is used to detect the presence of this target chemical.

The chemical sensor is embedded into the mobile phone case, such that when the mobile phone case is coupled the mobile device, the chemical sensor is aligned with flash of the camera of the mobile device. The chemical sensor filters light received from the flash of the camera unit of the mobile device and outputs the light at an analyzing unit embedded in the mobile phone case. A first end of the referencing arm and the sensing arm are coupled to the light source and receive light at the same intensity level. A second end of the referencing arm and the sensing arm output light at the analyzing unit. The intensity of the light output at the analyzing unit can vary from the referencing arm and the sensing arm.

The referencing arm includes Bragg gratings in its fiber core. The Bragg gratings have a uniform positive-only index change structure. The sensing arm includes a first Bragg grating and a second Bragg grating in its fiber core. The first Bragg grating has a period of a few hundred nanometers and is sensitive to carbon monoxide. The second Bragg grating has a long period structure in the order of hundreds of microns and is sensitive to nitrogen oxide.

The sensing arm is coated with two ligands, a heme-based ligand (iron) to detect carbon monoxide and a copper based ligand to detect nitrogen oxide. The coatings are specifically selected based on their respective ability to bond with molecules of carbon monoxide and nitrogen oxide. The coatings are applied at different portions of the sensing arm. The coating for carbon monoxide is applied over the area of the sensing arm having Bragg gratings with average periods. The coating for nitrogen oxide is applied over the area of the sensing arm having Bragg gratings with long periods. If either or both, carbon monoxide and nitrogen oxide are present in the environment the mobile device is exposed to, the surface of the sensing arm, coated with the ligand with bond with molecules of these pollutants.

An individual carries the mobile device into a constructions site to test for chemicals and/or gases present. The construction area contains levels of nitrogen oxide of which the individual is previously unaware. When the individual enters the construction area, the molecules of nitrogen oxide bond with the surface of the coated sensing arm of the chemical sensor embedded into the mobile device. The bonding of molecules of nitrogen oxide with the surface of the sensing arm results in a change in the intensity of the light transmitted through the sensing arm. The referencing arm is not coated and does not bond with molecules of the nitrogen oxide and the intensity of light transmitted through the referencing arm does not change when the individual enters the construction area.

The analyzing unit in the chemical sensor detects a difference in the intensity of light output by the sensing arm as compared to the referencing arm. The analyzing unit determines that the difference falls above a threshold value. The threshold value is sued to determine that the air is "dirty" and which target chemical is present. The analyzing unit compares the detected intensity values to a table of stored values indicating predicted intensity values for clean environments and dirty environments containing specific target chemicals. The chemical sensor determines that one of the target chemicals, nitrogen oxide, is present in the environment around the mobile device and the individual. In response to detecting the nitrogen oxide, the chemical sensor communicates with a microprocessor of the mobile device. The chemical sensor instructs the mobile device to vibrate and flash a warning on a user interface of the mobile device to warn the individual of the presence of the nitrogen oxide.

The examples demonstrate that by using a chemical sensor embedded into a mobile device or adaptable to a mobile device, an individual can detect various chemicals and/or gases in many different environments easily. The minimal size of the chemical sensor according to the embodiments discussed herein allows for use of the chemical sensor in many different applications without adapting or altering the chemical sensor. The chemical sensor is adaptable to many different environments, including an individual's home, an outdoor park, an office building, or any other suitable environment. The same sensor that can be used to detect various allergens in the environment around the individual, can be used to verify the safety of a worksite.

One or more flow diagrams may have been used herein. The use of flow diagrams is not meant to be limiting with respect to the order of operations performed. The herein described subject matter sometimes illustrates different components contained within, or connected with, different other components. It is to be understood that such depicted architectures are merely illustrative, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (for example, "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (for example, the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A system for detecting a target chemical, the system comprising:
  a chemical sensor configured to filter light, the chemical sensor comprising:
    at least one referencing arm configured to output light at a first intensity level; and
    at least one sensing arm sensitive to a target chemical, the at least one sensing arm configured to output light at a second intensity level;
  wherein the at least one sensing arm and the at least one referencing arm further comprise at least one Bragg grating configured to reflect particular wavelengths of light and transmit non-reflective wavelengths; and
  wherein the at least one sensing arm comprises a first portion with a first Bragg grating and a second portion with a second Bragg grating, wherein the first Bragg grating is sensitive to a different chemical target than the second Bragg grating, and wherein the first Bragg grating has a different period than the second Bragg grating.

2. The system of claim 1, wherein a surface of the at least one sensing arm comprises a coating configured to bind with a molecule of the target chemical, and wherein the presence of the target chemical changes a refractive index of the at least one sensing arm.

3. The system of claim 1, wherein a surface of the at least one sensing arm comprises a coating configured to fluorescence in the presence of the target chemical.

4. The system of claim 1 further comprising:
  a light source configured to transmit light through the at least one referencing arm and the at least one sensing arm; and
  an analyzing unit configured to detect the presence of the target chemical in response to comparing the first intensity level output by the at least one referencing arm to the second intensity level output by the at least one sensing arm.

5. The system of claim 1, wherein the target chemical comprises at least one of a volatile organic compound, a pollutant, and radon.

6. The system of claim 1, wherein the chemical sensor is embedded into a mobile phone case.

7. The system of claim 1, further comprising a mobile phone, wherein the mobile phone comprises:
  a light source configured to transmit light through the at least one referencing arm and the at least one sensing arm; and
  an analyzing unit configured to detect the presence of the target chemical in response to comparing the first intensity level output by the at least one referencing arm to the second intensity level output by the at least one sensing arm.

8. A method of detecting a target chemical, the method comprising:
  transmitting, by a light source, light through a chemical sensor, wherein the chemical sensor comprises a referencing arm and a sensing arm, wherein the sensing arm comprises a first portion with a first Bragg grating and a second portion with a second Bragg grating, wherein the first Bragg grating is sensitive to a different chemical target than the second Bragg grating, and wherein the first Bragg grating has a different period than the second Bragg grating;
  outputting, by the referencing arm, light at a first intensity level;
  outputting, by the sensing arm, light at a second intensity level, wherein the sensing arm is sensitive to a target chemical;
  comparing, by an analyzing unit, the first intensity level and the second intensity level; and
  detecting, by the analyzing unit, a presence of the target chemical based on a difference between the first intensity level and the second intensity level.

9. The method of claim 8, wherein the referencing arm is sensitive to temperature and pressure of an environment to which the chemical sensor is exposed, and wherein the sensing arm is sensitive to temperature, pressure, and the target chemical of an environment to which the chemical sensor is exposed.

10. The method of claim 8, further comprising binding, by a surface of the sensing arm, to a molecule of the target chemical, wherein the surface of the sensing arm comprises a coating, and wherein the presence of the target chemical changes a refractive index of the sensing arm.

11. The method of claim 8, further comprising applying a coating to a surface of the sensing arm, wherein the coating is configured to fluorescence in the presence of the target chemical.

12. The method of claim 8, wherein the sensing arm and the referencing arm further comprise a Bragg grating to reflect particular wavelengths of light and transmit the remaining wavelengths of light.

13. The method of claim 8, further comprising embedding the chemical sensor into a mobile phone case.

14. A method of preparing a chemical sensor, the method comprising:
creating a chemical sensor configured to filter light, wherein creating the chemical sensor comprises:
embedding a referencing arm into the chemical sensor, the referencing arm configured to output light at a first intensity level; and
embedding a sensing arm into the chemical sensor, the sensing arm sensitive to a target chemical, the sensing arm configured to output light at a second intensity level;
wherein the sensing arm comprises a first portion with a first Bragg grating and a second portion with a second Bragg grating, wherein the first Bragg grating is sensitive to a different chemical target than the second Bragg grating, and wherein the first Bragg grating has a different period than the second Bragg grating.

15. The method of claim 14, further comprising coating a surface of the sensing arm, wherein the coating is configured to bind with a molecule of the target chemical, and wherein the presence of the target chemical changes a refractive index of the sensing arm.

16. The method of claim 14, further comprising coating a surface of the sensing arm, wherein the coating is configured to fluorescence in the presence of the target chemical.

17. The method of claim 14, wherein the sensing arm and the referencing arm further comprise a Bragg grating configured to reflect particular wavelengths of light and transmit non-reflective wavelengths.

18. The method of claim 14 further comprising:
coupling a light source to the referencing arm and the sensing arm, wherein the light source is configured to transmit light through the referencing arm and the sensing arm; and
coupling an analyzing unit to the referencing arm and the sensing arm, wherein the analyzing unit is configured to detect the presence of the target chemical in response to comparing the first intensity level output by the referencing arm to the second intensity level output by the sensing arm.

19. The method of claim 14, further comprising embedding the chemical sensor into a mobile phone case.

20. The method of claim 14, wherein the system is a mobile phone, the method further comprising:
coupling a light source to the referencing arm and the sensing arm, wherein the light source is configured to transmit light through the referencing arm and the sensing arm; and
coupling an analyzing unit to the referencing arm and the sensing arm, wherein the analyzing unit is configured to detect the presence of the target chemical in response to comparing the first intensity level output by the referencing arm to the second intensity level output by the sensing arm.

* * * * *